(12) United States Patent
Bowen et al.

(10) Patent No.: US 6,638,588 B1
(45) Date of Patent: Oct. 28, 2003

(54) PERMEABLE MEMBRANES HAVING HIGH TEMPERATURE CAPABILITIES

(75) Inventors: William E. Bowen, Oregon, WI (US); Michael Stecker, Appleton, WI (US)

(73) Assignee: Pechiney Emballage Flexible Europe (FR)

( * ) Notice: Subject to any disclaimer, the term of this patent is extended or adjusted under 35 U.S.C. 154(b) by 0 days.

(21) Appl. No.: 09/594,679

(22) Filed: Jun. 16, 2000

(51) Int. Cl.[7] .............................. A61L 9/12; B32B 7/06
(52) U.S. Cl. ................... 428/35.7; 206/484; 206/484.1; 428/353; 428/354; 428/317.7; 428/474.4; 428/476.1; 428/476.9; 428/480; 428/483
(58) Field of Search ................. 428/35.2, 35.7, 428/354, 346, 353, 308.4, 317.1, 317.7, 319.3, 474.4, 476.1, 476.9, 483, 480; 206/484, 484.1; 239/56, 58

(56) References Cited

U.S. PATENT DOCUMENTS

| | | | |
|---|---|---|---|
| 3,216,882 A | 11/1965 | Feldt et al. | 161/109 |
| 3,858,807 A | 1/1975 | Rabussier et al. | 239/56 |
| 4,254,910 A | 3/1981 | Martin | 239/60 |
| 4,511,520 A | * 4/1985 | Bowen | 264/22 |
| 4,817,868 A | 4/1989 | Cook et al. | 239/55 |
| 5,071,704 A | 12/1991 | Fischel-Ghodsian | 428/354 |
| 5,296,291 A | * 3/1994 | Mueller | 428/349 |
| 5,518,790 A | 5/1996 | Huber et al. | 428/35.2 |
| 5,686,126 A | * 11/1997 | Noel et al. | 426/127 |
| 5,714,107 A | * 2/1998 | Levy et al. | 264/289 |
| 5,782,409 A | 7/1998 | Paul | 239/56 |
| 5,804,264 A | 9/1998 | Bowen | 428/35.2 |

FOREIGN PATENT DOCUMENTS

| | | | |
|---|---|---|---|
| JP | 02274529 A | * | 11/1990 |
| JP | 06199386 A | * | 7/1994 |

* cited by examiner

Primary Examiner—Sandra M. Nolan
(74) Attorney, Agent, or Firm—McDermott, Will & Emery

(57) ABSTRACT

A multilayer permeable film structure having high temperature capabilities comprising a first, perforated sealable layer; a second primer layer and a third outer layer is disclosed. The multilayer permeable film structure can be heat sealed to a formed tray containing a volatile material.

14 Claims, 1 Drawing Sheet

- LDPE/1.1 MILL COATING
- PEI PRIMER
- PERFORATED SEALABLE PET

- LDPE/1.1 MILL COATING
- PEI PRIMER
- PERFORATED SEALABLE PET
- SEALABLE PET COATING
- ALUMINUM TRAY FLANGE (SEAL AREA)
- ALUMINUM TRAY WITH FORMED CAVITY

PERMEABLE MEMBRANES HAVING HIGH TEMPERATURE CAPABILITIES

FIELD OF THE INVENTION

The invention pertains generally to the field of permeable membranes and packaging for volatile materials such as insecticides and other organic products. It pertains more particularly to permeable multilayer membranes having high temperature capabilities and also to packages incorporating such membranes, which allow for the controlled release of volatile materials over a period of time. The packages contain the volatile materials and prevent any substantial release of the volatile materials until heat has been applied to the packages.

BACKGROUND OF THE INVENTION

The controlled time release of more volatile substances, such as fragrances and other aromatic products, present a number of packaging problems. Room "air fresheners" or fragrances have usually been packaged in glass bottles or vials. The fragrance is released into the atmosphere by transmission through an absorbent wick, which is capped until the time of use. However, glass bottles are bulky and breakable. It is generally not economical to package fragrances in small quantities inside glass containers, because the cost of the glass container is high.

One proposed alternative method of packaging room fragrances involves placing a breakable glass vial within a plastic container formed of a material that is permeable to the vapors of the volatile fragrance. The user deliberately breaks the glass vial to allow the fragrance liquid to seep into an absorbent pad and the vapors from the liquid slowly diffuse into the atmosphere through the permeable outer container. These containers may be subject to accidental breakage of the glass vial during shipping and handling, as well as to possible puncture of the container by broken glass. The manufacturing costs are increased by the use of the glass vial within the container.

Other fragrance dispensers utilize sealed packages, which are opened by peeling back a covering foil to expose a perforated panel covering an absorbent pad saturated with the fragrance liquid. The costs of such containers make them generally inappropriate for dispensing small amounts of the fragrance. For such containers it is also somewhat difficult to control the release of the fragrance at a fairly constant rate over the life of the product, because the liquid is directly exposed to the atmosphere. Also, the consumer may contact the fragrance liquid itself, because the liquid may seep through the holes in the perforated panel.

DESCRIPTION OF THE ART

Rabussier, et al., U.S. Pat. No. 3,858,807 discloses an apparatus which is adapted for emitting vapors of volatile insecticidal agents or of similar volatile active liquid products such as insect repellants comprising a body made from a single fibrous plate or a stack of fibrous plates capable of absorbing the agent or product. The body is coated on at least one of its larger, principal outer faces with a diffusion layer of polymeric material diffusable by the said agent or product so as to emit vapors of the latter from the outer surface of the layer; the layer adheres on its inner side intimately to the fibers of the adjacent face of the fibrous plate to which it is applied. The apparatus further comprises a frame of metal or synthetic thermoplastic or the like material impervious to the volatile agent or product or to its vapors and sealing the body hermetically on all sides except the face or faces thereof which are coated with a diffusion layer where the frame has a window or windows; the layer is hermetically sealed along its periphery to the frame.

Holzner, U.S. Pat. No. 4,634,614 relates to a peel system for a device for perfuming ambient air. The peel system comprises a delamination of a paper layer to separate a non-permeable lidding from a permeable membrane.

Weyenberg et al., U.S. Pat. No. 4,145,001 discloses a dispenser having a permeable membrane. The fragrance is sandwiched between the inner layers of two heat sealable panels. One of the inner layers is permeable to the fragrance vapors. The outer layers of the panels are impermeable to the fragrance and its vapors. The dispenser is opened by peeling back a panel along a release layer to expose the inner permeable layer.

Martin, U.S. Pat. No. 4,254,910 discloses a packaging system for the controlled release of volatile substances. This packaging system comprises a pair of outer vapor-impermeable barrier layers and a vapor-permeable central layer which is bonded to each of the pair of vapor-impermeable outer layers, with the volatile material being contained between the central vapor-permeable layer and each of the outer vapor-impermeable barrier layers. The central vapor-permeable layer is formed from a pair of vapor-permeable webs which are bonded to one another.

Fischel-Ghodsian, U.S. Pat. No. 5,701,704 discloses a controlled release device useful for the release of vapors or liquids is described. The device is a multilayered laminate consisting of a reservoir layer which incorporates an active compound, such as a perfume or fragrance or insect repellant, an impermeable membrane layer adjacent the reservoir layer and a diffusion rate limiting membrane layer adjacent the reservoir layer.

Paul, U.S. Pat. No. 5,782,409 discloses sealing odor absorbing material and fragrance producing compositions separately in a flexible container, preferably formed from multi-layered sheet material. In the preferred embodiment, the odor absorbing material is retained by at least one microprobes or permeable membrane to prevent unwanted dispersion of the odor absorbing material into the ambient surroundings, while also controlling the rate of transfer of the ambient air into contact with the odor absorbing material.

Huber, U.S. Pat. No. 5,518,790 discloses a container to hold aromatic substances which can be sealed aroma-tight with a composite film consisting of several laminae. The composite film on the top of the container is made up of an aroma-tight outer film having at least two laminae and an aroma-permeable inner film which is detachably bonded to the outer film by means of a bonding agent. The outer film can be applied onto the inner film or membrane film, which consists of at least two permanently bonded laminae, whereby the lamina adhering to the container is made of polyethylene and the third or top lamina is made of a polymer material which has a different density.

Cook, U.S. Pat. No. 4,817,868 discloses a dispenser for broadcasting a scent which is particularly useful in connection with insect pheromones, a quantity of volatile pheromone carrying substance is packaged as a solid or gel in a hollow tube. A carrier can be provided for the tube, having a surface to which the tube is to be affixed with the longitudinal axis of the tube substantially parallel to the surface of the carrier, and the tube being disposed directly on the surface of the carrier. The carrier has at least one air circulation opening aligned perpendicular to the longitudinal axis of the tube and one or more stops preventing relative displacement of the tube and the carrier. Preferably, the carrier is a one piece integrally molded thermoplastic panel, with retaining clasps projecting from a planar body and adapted to bear diametrically inwardly on the tube. The length of the tube and dimensions of the carrier are such that the tube positively remains captive. Users are provided with substantially marginal area on the planar body adjacent the tube for manual manipulation, as needed, for example, to install the scent dispenser in a trap.

Despite the considerable art which is known, problems associated with permeable membranes still exist. One of these problems is the membrane's inability to maintain release product over long periods of time when subjected to temperatures above about 125° F. Therefore, in the field of permeable membrane and packaging for volatile products, especially insecticides, there is a need for a permeable membrane which is able to withstand such temperatures while providing control release of product over long periods of time.

One objective of the present invention is to provide a permeable multilayer membrane that has high temperature capabilities and a long-term release rate of volatile product. Another objective is to provide a multilayer permeable membrane, which allows for the selection of resins in its composition to bind to a container capable of holding volatile product but yet be able to withstand temperatures above about 125° F. A still further objective of the present invention is to provide packaging for volatile products, especially insecticides wherein said package can withstand temperatures above about 125° F. but yet be able to release product over a long period of time.

SUMMARY OF THE INVENTION

This invention relates to a permeable membrane for volatile materials, especially insecticides that satisfies the need for a permeable membrane having high temperature capabilities and that provides controlled release of product over a long period of time (7–30 days). This invention also relates to a package comprising a permeable membrane and a formed tray wherein said package is able to withstand temperatures between about 125° F. and about 300° F.

In one embodiment of the present invention, the invention is a multilayer structure comprising a permeable membrane. The membrane comprises a first permeable perforated sealable layer, a second primer layer and a third outer layer. The first perforated sealable layer is heat sealed to the formed tray containing the volatile product. The second primer layer is sandwiched between the first permeable, perforated sealable layer and the outer third layer and bonds the first and third layer together. The bond strength of layer two is sufficient to prevent delamination of the first and third layer during exposure to temperatures over 125° F. The outer third layer comprises a polymer which allows for permeation of the product but at the same time prevents undesired spillage of the product. Permeation of the third layer is determined by the polymer and/or thickness of the layer. The thickness of the outer third layer can range from 0.5 mls to 5 mls, preferable 1.0 mls to 3 mls.

The first permeable perforated sealable layer comprises a polymer or a blend of polymers wherein the polymer is selected from the group consisting of polyethylene terephthalate (PET), oriented poly(propylene) (OPP), and nylons wherein said nylons include poly($\epsilon$-caprolactam)/Nylon 6 and poly(hexamethylene)/Nylon 6,6. The first perforated sealable layer is a single layer film that has been perforated by conventional means known in the art. The percentage of perforation is determined by the desired permeation rate. The first, perforated sealable layer is then coated with a primer layer comprising an adhesive promoter. Adhesive promoter means a material which is capable of forming a strong bond between layers and is activated by heat. In the present invention the adhesive promoter is activated by the extrusion temperature of the third layer polymer.

A third layer, described below, is extruded onto the second primer layer. The resultant permeable membrane film structure from the third layer through the first perforated sealable layer is heat-sealed to the formed tray.

The second layer comprises a polymer that provides a strong bond between the first and third layer. The polymer for the second primer layer is an adhesive promoter which is exemplified by polyethylenimine. The polymer of the second layer is capable of forming a strong bond between the first and third layers. The bond strength which is provided by the above-described polymer is sufficient to prevent separation or delamination of the first and third layer, especially during exposure to temperatures above 125° F.

The outer third layer comprises a polymer or a blend of polymers wherein the polymer is selected from the group consisting of polyethylene, low density polyethylene, high density polyethylene, medium density polyethylene, ethylene vinyl acetate copolymer (EVA) or ethylene methyl acrylate copolymer (EMA). This layer is extruded on to the second layer.

Perforation shall mean a hole or pattern of holes made by piercing, boring or flame perforation. In the present invention the percentage of perforation is expressed by the number of holes per square inch and the diameter of each hole. The percentage of perforation for a given film layer is determined by the volatility of the product and the desired release time.

In another preferred embodiment of the present invention, the multilayer permeable membrane is incorporated into a package. The package holds the volatile material in a formed tray, and the multilayer permeable membrane is heat sealed to the formed tray. A formed tray suitable for practice in the present invention comprises a formed aluminum foil cavity which contains the volatile product, an aluminum foil tray flange and a PET/seal copolymer polyester which is coated onto the aluminum foil tray flange. The package can then be placed in a heating device. While the permeable membrane of the present invention has been described as being heat-sealed to an aluminum foil tray, it is also contemplated that the tray could also be produced from a thermoformable polymeric film.

The package of this invention has the desirable feature of being relatively light in weight while having no breakable parts that might be hazardous. The package is inexpensive to manufacture and is suitable for dispensing small quantities of material. The package can be heated to temperature between about 125° F. to about 300° F. without failure of the permeable membrane. Once the package has been placed in a heater, the volatile vapors diffuse through the permeable membrane at a controlled rate. Because this transfer of the vapors through the permeable layer is a diffusion process rather than direct evaporation, the rate of release of the product is relatively uniform over the expected life of the package. The package also provides a controlled release rate of about 7 to about 30 days.

In a preferred process for producing the package, the permeable membrane is produced by first coating an adhesive/primer onto the perforated sealable film layer, then extruding a polymer onto the adhesive primer layer, and lastly, heat sealing this permeable membrane to a formed tray.

While the package of the present invention has been described as having a permeable membrane comprising three layers which is heat sealed to a formed tray, other embodiments are contemplated. For example, the package of the present invention could also comprise an impermeable portion wherein said portion could comprise one or more layers. The impermeable portion could further comprise a release layer wherein said release layer can be laminated to the impermeable portion opposite the permeable membrane. The release layer is comprised of a polymer which is relatively impermeable to the product and supports the impermeable layers in containing the product.

BRIEF DESCRIPTION OF THE DRAWING

The invention will be further described in connection with the accompanying drawings, in which.

DETAILED DESCRIPTION OF THE DRAWINGS

Figure 1:
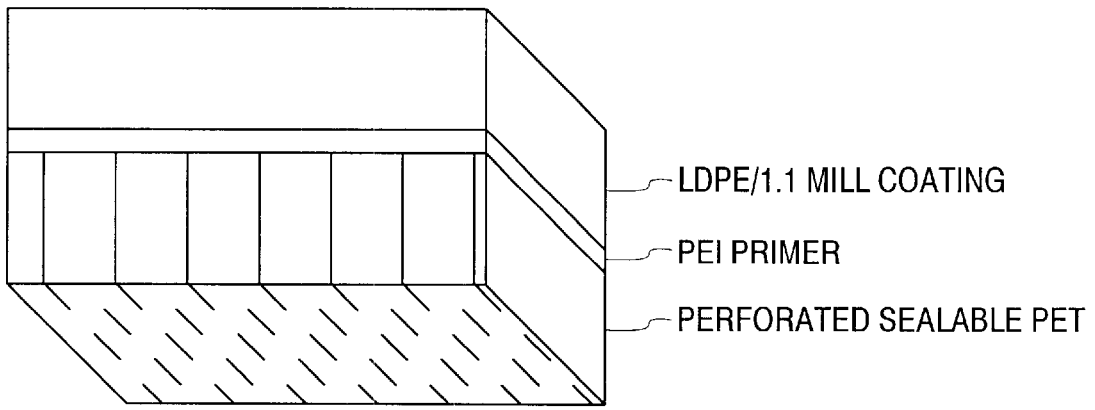
FIG. 1 is a cross-section of an embodiment of a multilayer structure of this invention.

Referring to the drawings, an embodiment of the invention is shown generally in FIG. 1. The multilayer structure comprises a first perforated sealable layer (20), a second primer layer (22) sandwiched between said first layer and a third layer and said third layer (24). The second layer is coated onto the first, perforated sealable layer and the third layer is extruded on to the second primer layer to form the permeable membrane structure.

Layer (20) is permeable and cooperates with layers 22 and 24 providing the desired permeability of the membrane. Layer 20 comprises polymers and other components that provide good permeability properties and good heat seal properties. Examples of materials that are suitable for layer 20, included polyethylene terephthalate (PET), oriented polypropylene (OPP), and nylons wherein said nylons include poly(ε-caprolactam)/Nylon 6 and poly (hexamethylene)/Nylon-6,6. The polymer that comprises layer 20 is extruded into a single layer film wherein said film is perforated by conventional means known in the art. The percentage of perforation is determined by the desired rate of permeation. A particularly preferred polymer for layer 20 is 60 Ga PET/seal copolymer polyester with a perforation of 330 holes per square inch and wherein the diameter of each hole is 0.7 mm, which is supplied by EPL Flex Packaging Corporation which perforates the film which is supplied by Dupont (Dupont/ICI 851).

Layer 22 is a permeable primer layer that forms a strong bond between layer 20 and 24. An example of a material that is suitable for layer 22 is polyethylenimine. The bond strength which is provided by the adhesive primer polymer of layer 22 is sufficient to prevent separation or delamination of layers 20 and 24. A particularly preferred polyethylenimine is Mica-A-131-X from Mica Corporation.

Layer (24) is permeable and cooperates with layers (20) and (22) to provide the desired permeability of the membrane. Layer (24) comprises polymers and other components that provide good permeability. Examples of materials that are suitable for layer 24 include polyethylenes, low density polyethylenes, high density polyethylenes and medium density polyethylenes. A particularly preferred polymer is low density polyethylene (LDPE). A particularly preferred LDPE is Equistar NA-204 from Equistar Chemicals of Clinton, La. Layer 24 is extruded on to layer 22 to form the permeable membrane structure of the present invention.

Figure 2:
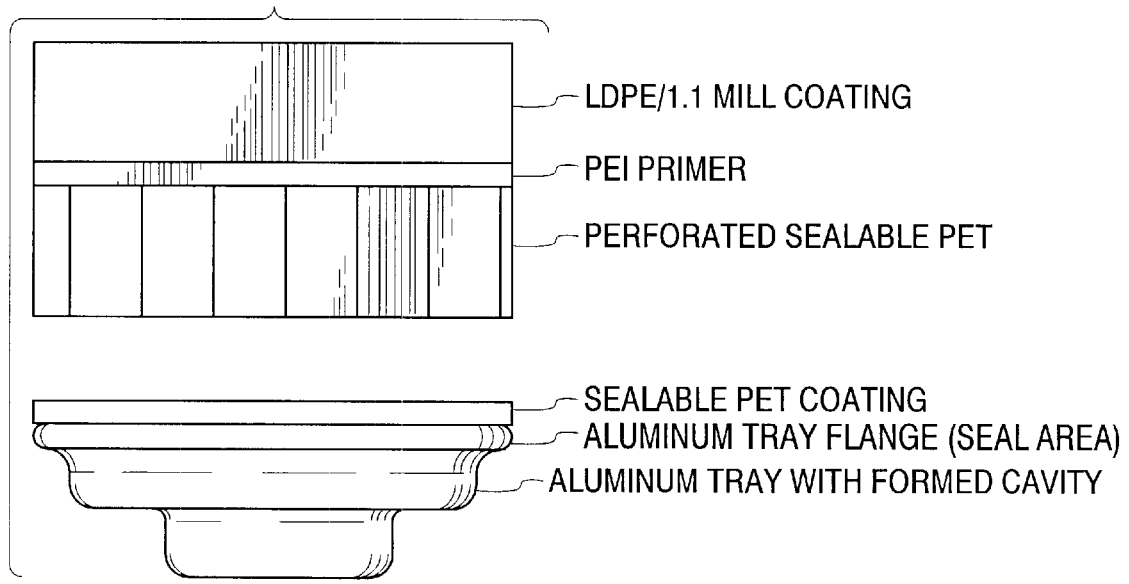
FIG. 2 is a cross-section of a package, in accordance with this invention.

FIG. 2 shows the incorporation of a preferred multilayer permeable membrane of the present invention into a package containing volatile materials, especially an insecticide. The package comprises two parts, the multilayer permeable membrane and a formed tray. The outer layer of the formed tray comprises an aluminum foil which has been coated with sealable polyester. The perforated, sealable layer of the multilayer permeable membrane is heat sealed to the sealable polyester layer of the formed tray. The package can then be placed in a heating device for use.

The following example is provided as illustrative of the invention, but should not be construed as being exhaustive or as limiting the invention to the specific details thereof.

EXAMPLE 1

A multilayer structure according to the invention was produced as follows: a first heat sealable, perforated film layer having a perforation percentage of 330 holes per square inch with a per hole diameter of 0.7 mm was coated with polyethylenimine. Low density polyethylene was extruded onto this film structure. The resultant permeable membrane was then heat sealed to a formed aluminum foil tray. In Example 1, the perforated film layer was 60 Ga Perforated PET/seal copolymer polyester, wherein the polymer is Dupont/ICI 851 and the final perforation film is Mica-A-131-X from Mica Corporation. The LDPE is Equistar NA-204 from Equistar Chemicals.

What is claimed is:

1. A package comprising a permeable membrane and a formed tray wherein the permeable membrane consists essentially of:
   (d) a first permeable perforated sealable layer wherein said layer comprises a polymer or a blend of polymers wherein the polymer is selected from the group consisting of polyethylene terephthalate, oriented poly (propylene) and nylons;
   (e) a second primer layer; and
   (f) a third outer layer.

2. A permeable membrane having high temperature capabilities for the release of a volatile product wherein the membrane consists essentially of:
   (a) a first permeable perforated scalable layer wherein said layer comprises a polymer or a blend of polymers wherein the polymer is selected from the group consisting of polyethylene terephthalate, oriented poly (propylene) and nylons;
   (b) a second primer layer; and
   (c) a third outer layer.

3. The permeable membrane according to claim 2 wherein the nylon is selected from poly(ε-caprolactam) and poly (hexamethylene adipamide).

4. The permeable membrane according to claim 2 wherein said second primer layer comprises a polymer that provides a strong bond between the first and second layers.

5. The permeable membrane according to 2 claim wherein said third outer layer comprises a polymer selected from the group consisting of polyethylene, low density polyethylene, high density polyethylene and medium density polyethylene.

6. The permeable membrane according to claim 2 wherein said membrane is capable of withstanding temperatures between about 125° F. to about 300° F.

7. The permeable membrane according to claim 2 wherein the polyethylene terephthalate is perforated.

8. The permeable membrane according to claim 7 wherein the perforation is about 330 holes per square inch with a diameter of about 0.7 mm per hole.

9. The permeable membrane according to claim 2 wherein the second primer layer is coated on to the first permeable, perforated sealable layer.

10. The permeable membrane according to claim 2 wherein the third outer layer is extruded onto the second primer layer.

11. The permeable membrane according to claim 2 wherein the first permeable, perforated sealable layer is heat sealed to a formed tray.

12. The permeable membrane according to claim 5 wherein the polymer is low density polyethylene.

13. A permeable membrane having high temperature capabilities for the release of a volatile product wherein the membrane comprises:
 (a) a first permeable perforated sealable layer wherein said layer comprises a polymer or a blend of polymers wherein the polymer is selected from the group consisting of polyethylene terephthalate, oriented poly (propylene) and nylons;
 (b) a second primer layer comprising a polymer that provides a strong bond between the first and third layer wherein said polymer is polyethylenimine; and
 (c) a third outer layer.

14. A package having high temperature capabilities wherein said package comprises a permeable membrane according to claim 13 and a formed tray.

* * * * *